US00PP33923P2

(12) United States Plant Patent
Ranney et al.

(10) Patent No.: US PP33,923 P2
(45) Date of Patent: Feb. 1, 2022

(54) AZALEA PLANT 'NCRX7'

(50) Latin Name: ***Rhododendron* hybrid**
Varietal Denomination: NCRX7

(71) Applicant: North Carolina State University, Raleigh, NC (US)

(72) Inventors: Thomas Green Ranney, Arden, NC (US); Darren Touchell, Raleigh, NC (US); Irene Palmer, Raleigh, NC (US); Andra Nus, Raleigh, NC (US); Nathan P. Lynch, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 17/343,174

(22) Filed: Jun. 9, 2021

(51) Int. Cl.
*A01H 6/38* (2018.01)
*A01H 5/00* (2018.01)

(52) U.S. Cl.
USPC ..... Plt./240

(58) Field of Classification Search
USPC ..... Plt./240
See application file for complete search history.

*Primary Examiner* — Annette H Para
(74) *Attorney, Agent, or Firm* — Cassandra Bright

(57) ABSTRACT

A new and distinct cultivar of *Rhododendron* plant named 'NCRX7' having prolific, large, semi-double, deep pink flowers, a compact (mid-sized) habit, cold hardiness to USDA Zone 6b, and consistent Fall reblooming.

2 Drawing Sheets

Latin name of the genus and species: The Latin name of the novel plant variety disclosed herein is *Rhododendron* hybrid.

Variety denomination: 'NCRX7'.

The inventive hybrid was selected from seedlings derived from a controlled cross between evergreen azalea hybrids 'Sky Hill Pose' (unpatented, female) and 'Fourth of July' (unpatented, male). Prior to the designation of the varietal denomination, 'NCRX7' was referred to by its experimental code: H2013-168-035.

BACKGROUND OF THE INVENTION

The present invention comprises a new and distinct hybrid evergreen azalea cultivar hereinafter referred to by the cultivar name 'NCRX7'. This hybrid azalea was developed by a controlled breeding program at North Carolina State University, in Mills River, N.C. 'NCRX7' was selected for its large, prolific, semi-double, deep pink flowers, moderate and dense growth habit, and consistent reblooming in Fall. 'NCRX7' was obtained from the controlled, hand pollination of emasculated female *Rhododendron* 'Sky Hill Pose' (unpatented) and male/pollen parent *Rhododendron oldhamii* 'Fourth of July' (unpatented). 'NCRX7' was selected from this population after 6 years in trials at the Mountain Horticultural Crops Research and Extension Center in Mills River, N.C.

Container trials were conducted using pine bark media supplemented with 1.04 $kg \cdot m^{-3}$ dolomitic lime, 0.74 $kg \cdot m^{-3}$ granulated micronutrients (Micromax; ICL Specialty Fertilizers, Tel Aviv, Israel) and top-dressed with 5- to 6-month slow-release fertilizer (Osmocote Plus 15-9-12, ICL Specialty Fertilizers). Full-sun field trials were conducted in plastic-covered, bark-amended clay soils with minimum winter temperatures of −2° F. (−19° C.) and maximum summer temperatures 98° F. (37° C.). The first asexual propagation of 'NCRX7' occurred in 2015 by rooting stem cuttings at the North Carolina State University Mountain Horticultural Crops Research Station, Mills River, N.C.

'NCRX7' roots readily from firm softwood cuttings treated with a basal dip of 3,000-5,000 ppm indole-3-butyric acid (potassium salt) in water. 'NCRX7' has been found to retain its distinctive characteristics through successive asexual propagations over 6 years.

SUMMARY OF THE INVENTION

The following are the unique combination of characteristics of this new cultivar when grown under standard horticultural practices at North Carolina State University, Mountain Horticultural Crops Research Station, Mills River, N.C.

1. Prolific, large, semi-double, deep pink flowers.
3. Cold hardiness to USDA 6b.
4. Compact habit.
5. Consistent Fall reblooming.

COMPARISON WITH PARENTS

TABLE 1

| Plant | Flower Color | Flower Type | Habit |
|---|---|---|---|
| FEMALE: *Rhododendron* 'Sky Hill Rose' (unpatented) | RHS Red-Purple Group 57C | Semi-double | Hardiness: USDA 6b<br>Mature Height × Width: 50 × 80 cm<br>Flower size: approximately 7 cm. |
| MALE: *Rhododendron* 'Fourth of July' (unpatented) | RHS Red Group 39A | Single | Hardiness: USDA Zone 7b<br>Mature Height × Width: 250-300 cm × 180-200 cm.<br>Flower size: 4-6 cm. |
| *Rhododendron* 'NCRX7' | RHS Red-Purple Group N66C | Semi-double | Hardiness: USDA Zone 6b<br>Mature Height × Width: 75 × 90-120 cm<br>Flower size: 5.5-7 cm. |

COMPARISON WITH COMMERCIAL CONTROLS

TABLE 2

| Plant | Flower Color and Type | Habit | Additional characters |
|---|---|---|---|
| *Rhododendron* 'Conlea' U.S. Plant Pat. No. 10,438 | Deep pink semi-double; petaloids present. RHS Red Group 54A | Large 180-240 × 120-150 cm | Hardy to Zone 7 |
| *Rhododendron* 'RLH1-2P8' U.S. Plant Pat. No. 21,477 | Bright pink, semi-double flowers, petaloids present; petals ruffled/petticoat-like flowers. RHS N57D | Mid-sized: 130 cm × 120 cm | Hardy to Zone 6 |
| *Rhododendron* 'Roblec' U.S. Plant Pat. No. 15,339 | Light pink semi-double flowers, petaloids present; petals ruffled/petticoat like flowers. RHS Red-Purple Group 73B | Mid-sized: 150 cm × 120 cm | Hardy to Zone 7 |
| *Rhododendron* 'NCRX7' | Dark pink semi-double; petaloids present. RHS Red-Purple Group N66C | Mid-sized to compact: 75 × 90-120 cm | Hardy to Zone 6b |

BRIEF DESCRIPTION OF THE DRAWINGS

'NCRX7' is illustrated by the accompanying photographs, which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Rhododendron*.

DETAILED BOTANICAL DESCRIPTION

Figure 1:
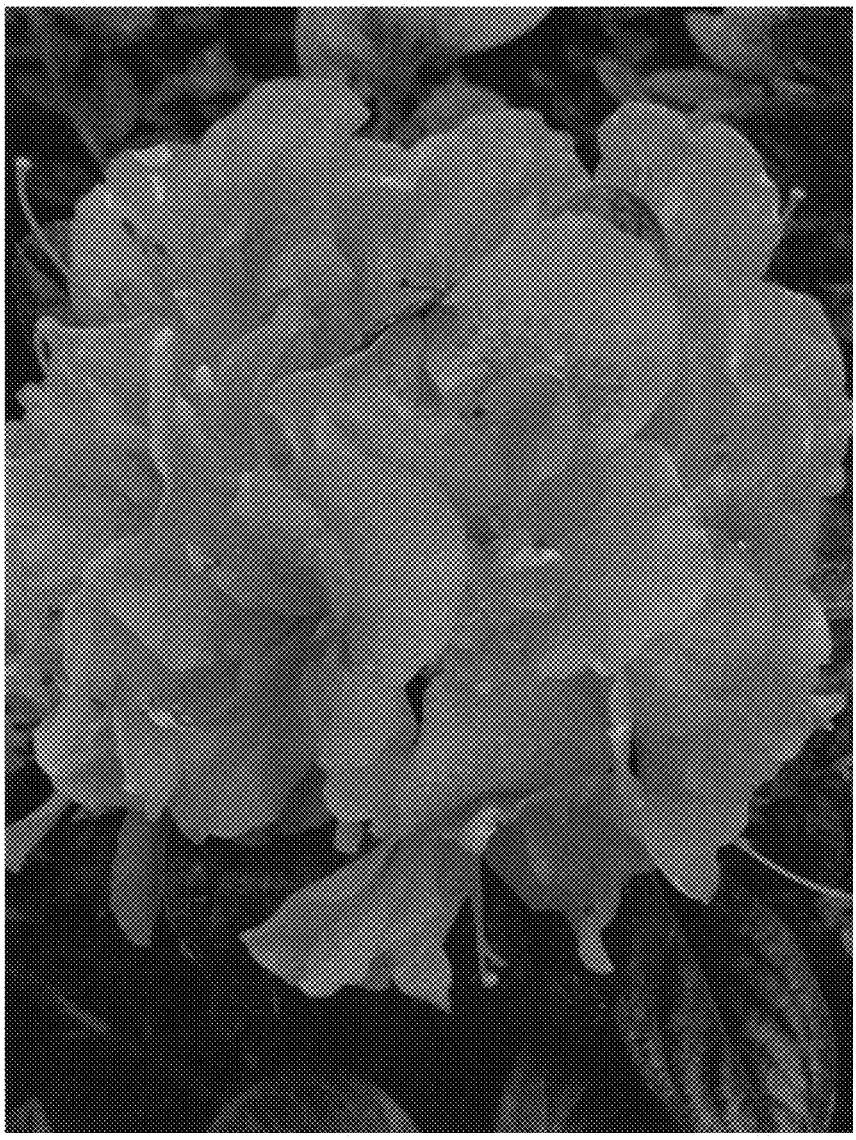
FIG. 1 illustrates fully expanded trusses with deep pink semi-double flowers on a 2-year-old container plant grown in Grand Haven, Mich., in 2020.
Figure 2:
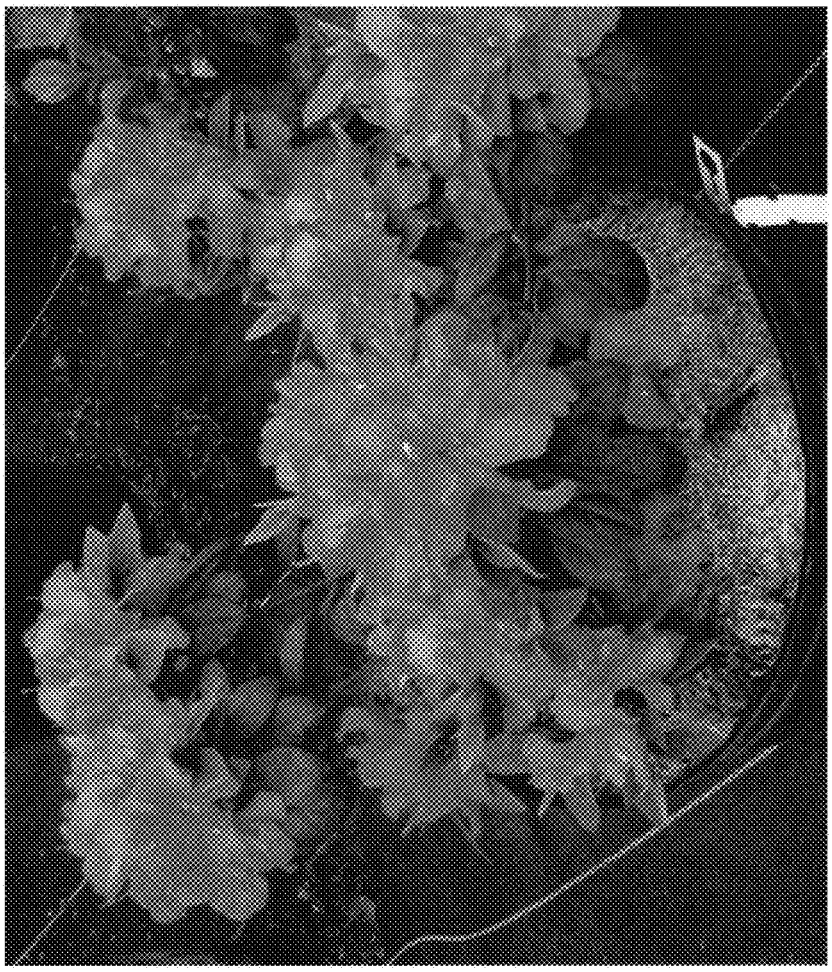
FIG. 2 illustrates the dense plant habit and form, as well high floral coverage on a 2-year-old container-grown plant in Grand Haven, Mich., in 2020.

The following is a detailed description of the botanical characteristics of the new and distinct hybrid evergreen azalea known by the denomination 'NCRX7'. The detailed description was taken on a 3-year-old container-grown plant in Mills River, N.C., in 2020. Where pertinent, descriptive data was supplemented by observations/measurements taken on a 5-year-old individual located in field trials in Mills River, N.C., as well as information provided from cooperators in Grand Haven, Mich. All colors cited herein refer to The Royal Horticultural Society Colour Chart (The Royal Horticultural Society (R.H.S.), London, 2015 Edition. Where specific dimensions, sizes, colors, and other characteristics are given, it is to be understood that such characteristics are approximations or averages set forth as accurately as is practicable.

Plant:

*Plant type*.—Evergreen flowering shrub.
*Growth habit/form*.—Globose, upward arching.
*Height at maturity*.—~75-100 cm.
*Width at maturity*.—~100-120 cm.
*Roots*.—Fibrous.
*Growth rate*.—Moderate.

Shoots and branches:

*Shoots* (*softwood new growth, current years growth*).—Shape: Rounded. Color: RHS Yellow-Green Group 144D. Texture: Pubescent. Pubescence color: RHS Greyed-Orange Group 165A. Shoot diameter: 1.3-3 mm. Shoot length: Variable, ranging from ~10-20 cm.

*Shoot* (*prior-years woody shoots*).—Shape: Rounded. Color: RHS Greyed-Orange Group 177A. Texture: Exfoliating, some pubescence. Pubescence color: RHS Greyed-Orange Group 177A. Stem diameter: Generally 3-6 mm. Stem length: Variable, ranging from 3-15 cm. Stem aspect: 0-90

*Branches* (*woody stems*).—Shape: Rounded. Color: RHS Greyed-Orange Group 177B. Texture: Gently exfoliating with some pubescence. Branch diameter: Approximately 5-8 mm. Branch length: Variable, approximately 10-25 cm. Branching: Freely branched. Number of lateral branches: Variable, 30-50.

Foliage:

*Type*.—Evergreen.
*Arrangement*.—Alternate.
*Division*.—Simple.
*Shape*.—Elliptic to obelliptic.
*Apex*.—Mucronate.
*Base*.—Cuneate.
*Margin*.—Entire, ciliate.
*Venation*.—Reticulate.
*Internode length*.—Approximately 5-15 mm.
*Immature leaf*.—Adaxial (upper) surface: Color: RHS Yellow-Green Group 144A. Surface: Pubescent. Pubescence color: RHS White Group N155B. Abaxial (lower) surface: Color: RHS Green Group 142B. Surface: Pubescent. Pubescence: RHS White Group N155B.
*Mature leaf*.—Length: Approximately 5-7 cm. Width: Approximately 2-3.5 cm. Color: Adaxial (upper) surface: RHS Green Group 139A. Abaxial (lower) surface: RHS Green Group N138B. Surface: Pubescent along midrib. Fall/Winter Color: Adaxial side: RHS Greyed-Purple Group N186A to N187A. Abaxial side: RHS Greyed-Orange Group 176B mixed with RHS Yellow-Green Group 148B.
*Leaf attachment*.—Petiolate.

Petiole:

*Shape*.—Lunate.
*Length*.—Approximately 6-10 mm.
*Diameter*.—Approximately 1-2 mm.
*Color*.—Adaxial/abaxial side: RHS Yellow-Green Group 145C. Surface: Both sides are pubescent. Pubescence color: RHS Greyed-Orange Group 163C.

Flower:

*Type*.—Congested terminal raceme (truss).
*Flowering season*.—Mid-Spring (Mid-April-May/June) reblooms in Early Fall (Late September through October).
*Flowering habit*.—Free-flowering.
*Flower number*.—2-4 per truss.
*Consistency in display*.—Blooms reliably in the spring and consistently reblooms in the fall.
*Lastingness of flowers*.—Each flower lasts approximately 3-7 days.
*Fragrance*.—None.
*Self-cleaning or persistent*.—Self-cleaning.

Truss bud:
- *Length*.—Approximately 15-25 mm.
- *Diameter*.—Approximately 6-12 mm.
- *Bud scales*.—Number: Variable: 5-8. Length: Approximately 13-20 mm. Width: Approximately 4-12 mm. Color prior opening: RHS Yellow-Green Group 145C fading to RHS Yellow-Green Group 146B at tip. Color after flowers emerge: RHS Yellow-Green Group 145D at base, transitioning to RHS Yellow-Green group 146D at the tip.
- *Texture*.—Adaxial side is glabrous; abaxial side is pubescent at tip.

Emerging flowers prior to opening:
- *Shape*.—Elliptic, acuminate.
- *Length*.—3-4 cm.
- *Diameter*.—5-15 mm.
- *Color*.—RHS Red-Purple Group 67C.

Perianth:
- *Diameter at anthesis*.—5.5-7 cm.
- *Depth*.—2.5-4 cm.
- *Organization*.—Petals are arranged in an outer whorl with a variable number of petals and anther- derived petaloids in an inner (complete or incomplete) whorl.
- *Aspect*.—Facing upwards and outwards.
- *Shape*.—Broadly funnel-shaped.
- *Attachment*.—Pedicellate.

Petals and petaloids: Generally, petals in the first whorl have similar dimensions and shapes, while petaloids vary significantly in size, shape, and number. Petals and petaloids are similar in color.
- *Petal/petaloid number*.—5 petals in the outer whorl with a variable number of 5-10 petals and anther-derived petaloids in the inner whorl.
- *Petal length*.—4-5 cm.
- *Petaloid length*.—2-4 cm.
- *Petal width*.—2-3 cm.
- *Petaloid width*.—0.5-2 cm.
- *Petal shape*.—Obovate.
- *Petaloid shape*.—Variable.
- *Petal apex*.—Undulate/obovate.
- *Petaloid apex*.—Variable.
- *Petal margin*.—Undulate.
- *Petaloid margin*.—Various. Petals fused at midpoint; petaloids generally unfused.
- *Petal/petaloid color*.—Color is consistent from opening to anthesis. Adaxial (upper) surface: RHS Red-Purple Group N66C. Surface: Smooth, silky. Blotch: RHS Red-Purple Group 60A. Abaxial (lower) surface: RHS Red-Purple Group 68B at base transitioning to RHS Red-Purple Group 67C at the midpoint to tip. Pigmentation lightens around the dorsal flare to RHS Red-Purple Group 68C. Surface: Smooth, silky.

Calyx/receptacle:
- *Shape*.—Star-shaped, single-whorl of persistent sepals.
- *Sepals*.—Number: 5. Length: 3-6 mm. Width: 2.5-4 mm. Shape: Lanceolate. Apex: Cuneate. Margin: Ciliate. Color: RHS Yellow-Green Group 145A. Surface: Adaxial side is glabrous; abaxial side is pubescent.

Pedicels:
- *Shape*.—Rounded.
- *Length*.—8-17 mm.
- *Diameter*.—1-2 mm.
- *Color*.—RHS Yellow-Green Group 145A at base, transitioning to RHS Yellow-Green Group 145C at the distal end.
- *Surface*.—Both sides are pubescent.

Reproductive organs: Most likely as an effect of anther-derived floral doubling, reproductive characters including style length, stigmatic surface dimensions, stamen number, filament length, and anther dimensions can be variable.

Gynoecium:
- *Pistil number*.—1.
- *Pistil length*.—5-6 cm.
- *Stigma shape*.—Orbicular to elliptic.
- *Stigma length*.—1-1.5 mm.
- *Stigma width*.—1-1.5 mm.
- *Stigma color*.—RHS Red-Purple Group 59A.
- *Style length*.—4.5-5.5 cm.
- *Style diameter*.—0.3-0.5 mm.
- *Style color*.—RHS Red-Purple Group 67D.
- *Ovary shape*.—Dome-shaped.
- *Ovary length*.—4-5 mm.
- *Ovary diameter*.—1.5-3 mm.
- *Ovary color*.—RHS Green Group 143A.
- *Surface*.—Tomentose, RHS White Group N155B.

Androecium:
- *Stamen number*.—Variable, 5 is common but more or less than 5 possible.
- *Anther shape*.—Ovoid with two apical pores.
- *Anther attachment*.—Dorsifixed.
- *Anther length*.—Approximately 2 mm.
- *Anther width*.—Approximately 1 mm.
- *Anther color*.—RHS Red-Purple Group 59C.
- *Filament length*.—3-5 cm.
- *Filament diameter*.—Approximately 0.5 mm.
- *Filament color*.—RHS Red-Purple Group 68C, transitioning to RHS Red-Purple Group 67C at the distal end.
- *Amount of pollen*.—Normal.
- *Pollen type*.—Vicinate.
- *Pollen color*.—RHS Yellow-White Group 158B.

Other characteristics:
- *Fruit type*.—Capsule.
- *Fruit texture*.—Pubescent.
- *Fruit length*.—Approximately 15 mm if successfully pollinated, ~7 mm if not.
- *Fruit diameter*.—Approximately 8 mm if successfully pollinated, ~4 mm if not.
- *Fruit color*.—RHS Brown Group 200D.
- *Seed number*.—Variable 0 to hundreds.
- *Seed length*.—Approximately 1 mm.
- *Seed diameter*.—Approximately 0.5 mm.
- *Seed color*.—RHS Yellow-Orange Group 22A.

Propagation: Roots readily (>90%) from firm, terminal, softwood stem cuttings taken in mid-summer. 'NCRX7' roots well when the bottom 2 cm of the stems are treated for 5 seconds with 3,000-5,000 ppm of potassium salt of indole-3-butyric acid (KIBA) dissolved in water and placed under intermittent mist for 8-10 weeks until roots form.

Disease and insect resistance: No significant disease or insect pests have been observed.

Cold hardiness: Has been reliably cold hardy in USDA 6b.

What is claimed is:

1. A new and distinct cultivar of *Rhododendron* plant named 'NCRX7' as herein illustrated and described.

* * * * *